United States Patent [19]

Schlatter

[11] 3,983,162
[45] Sept. 28, 1976

[54] OPTICAL RESOLUTION OF ALKYL ESTERS OF DL-PHENYLALANINE

[75] Inventor: James M. Schlatter, Glenview, Ill.

[73] Assignee: G. D. Searle & Co., Chicago, Ill.

[22] Filed: Jan. 2, 1975

[21] Appl. No.: 538,091

[52] U.S. Cl. .............................................. 260/471 A
[51] Int. Cl.² ............................................ C07C 99/12
[58] Field of Search ................................. 260/471 A

[56] References Cited
UNITED STATES PATENTS 3,832,388  8/1974  Lorenz ........................... 260/471 A Primary Examiner—Richard L. Raymond
Attorney, Agent, or Firm—John A. Dhuey

[57] ABSTRACT

Treatment of an alkyl ester of DL-phenylalanine with an N-acyl-D-phenylalanine results in the formation of the corresponding insoluble salt of L-phenylalanine alkyl ester and N-acyl-D-phenylalanine. The salt is purified by recrystallization in the presence of an added quantity of the alkyl ester of DL-phenylalanine or the alkyl ester of L-phenylalanine. The isolated, purified salt is decomposed to afford the desired L-phenylalanine alkyl ester, which is an important starting material in the preparation of artificial sweetening agents.

4 Claims, No Drawings

OPTICAL RESOLUTION OF ALKYL ESTERS OF DL-PHENYLALANINE

BACKGROUND OF THE INVENTION

Lower alkyl esters of L-phenylalanine are preferred starting materials in the manufacture of certain sweetening agents, as disclosed in U.S. Pat. No. 3,492,131. However, heretofore those starting materials have been difficult and expensive to obtain. Due to the absence of suitable asymmetric syntheses, prior art efforts have been directed most often to the resolution of the DL-compounds.

A process for resolving alkyl esters of DL-phenylalanine has been developed and disclosed in a copending application Ser. No. 395,940 of Paul B. Sollman, now U.S. Pat. No. 3,941,831, which utilizes, as intermediates, salts of the alkyl esters of L-phenylalanine and N-acyl-D-phenylalanines. Those salts are conveniently represented by the following formula

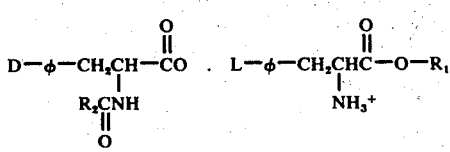

wherein $R_1$ is a lower alkyl radical having 1–4 carbon atoms inclusive and $R_2$ is hydrogen or a lower alkyl radical having 1–7 carbon atoms inclusive. The salts are useful intermediates in the preparation of the lower alkyl esters of L-phenylalanine. Illustrative of these alkyl radicals intended are methyl, ethyl, n-propyl, isopropyl, n-butyl, isobutyl, sec-butyl and tert-butyl.

Other art equivalent acyl blocking groups, both aliphatic and aryl, may be utilized for $r_2$, but the lower alkyl radicals described above are preferred.

The process is practiced preferably by contacting an alkyl ester of DL-phenylalanine in a suitable solvent with an N-acyl-D-phenylalanine; isolating and purifying the salt of the corresponding alkyl ester of L-phenylalanine and N-acyl-D-phenylalanine; decomposing the salt into its respective components; and isolating the desired alkyl ester of L-phenylalanine. The initial salt formation yields crude product which contains a quantity of undesired salt of the N-acyl-D-phenylalanine and D-phenylalanine alkyl ester.

The instant salt formation is most advantageous since it permits the N-acyl derivatives of D-phenylalanine to be utilized as the resolving agents, effecting substantial cost savings over the use of the L-isomer. Thus, the desired L-isomer of phenylalanine need not be tied up in the process. Furthermore, the crystallization of the D-L salts affords, upon purification decomposition and separation, pure product consisting of the appropriate alkyl ester of L-phenylalanine.

Typically, N-acetyl-D-phenylalanine is allowed to contact DL-phenylalanine methyl ester in a suitable solvent, e.g. methanol, ethylene chloride or water, to produce a crude crystalline salt of N-acetyl-D-phenylalanine and L-phenylalanine methyl ester. That salt is separated from the filtrate, purified and decomposed with aqueous hydrochloric acid to afford N-acetyl-D-phenylalanine as a precipitate and L-phenylalanine methyl ester hydrochloride in solution. After filtering, the solvent in the filtrate is removed to afford the hydrochloride salt of L-phenylalanine methyl ester.

Alternatively, the salt of N-acetyl-D-phenylalanine and L-phenylalanine methyl ester is dissolved in aqueous potassium carbonate and extracted with ether. The D-amide remains in the aqueous phase and the L-ester is extracted into the organic phase. After phase separation, the ethereal solution is acidified with hydrochloric acid-isopropanol to precipitate the hydrochloride salt of L-phenylalanine methyl ester.

It is apparent that the starting materials useful in the process may be employed as their equivalent salts. For example, the hydrochloride salt of DL-phenylalanine methyl ester may be utilized along with the sodium salt of N-acyl-D-phenylalanine.

DESCRIPTION OF THE INVENTION

The present invention is concerned generally with the purification of the salt of the alkyl ester of L-phenylalanine and the N-acyl-D-phenylalanine resolving agent. More particularly, it is concerned with an improved method for obtaining the aforementioned salt in substantially pure form in a single step.

It has been discovered, surprisingly, that substantially pure salt (i.e. greater than 97% optical purity) can be obtained by recrystallizing the impure salt in the presence of an added quantity of the alkyl ester of DL-phenylalanine or the alkyl ester of L-phenylalanine. In that manner, the crude salt (about 89–90% optical purity) is upgraded in one step to substantially pure salt greater than 97% optical purity. An added unobvious advantage of the instant improvement is that the quantity of desired salt is not diminished at the end of the recrystallization step.

Illustrative of the instant improvement are the results achieved by recrystallizing the salt formed by adding 0.55 moles of N-acetyl-D-phenylalanine to 1.0 mole of DL-phenylalanine methyl ester in ethylene chloride containing 5% methanol, which salt contains about 89% N-acetyl-D-phenylalanine. L-phenylalanine methyl ester and 11% N-acetyl-D-phenylalanine. D-phenylalaline methyl ester. The crude salt when slurried with 11% of L-phenylalanine methyl ester (percentage being based on the crude salt weight) in ethylene chloride gives 98% yield of the salt of N-acetyl-D-phenylalanine and L-phenylalanine methyl ester of 99% optical purity. Substitution of 22% DL-phenylalanine methyl ester for the 11% L-phenylalanine methyl ester gives 98% recovery of 98% optically pure salt of N-acetyl-D-phenylalanine and L-phenylalanine methyl ester.

In general the exact nature of the solvents utilized for the recrystallization are not critical since the salt may be either slurried or dissolved during the process. However, it will be appreciated that solvents which might react with and decompose the salt are to be avoided. Accordingly, solvents inert with respect to salt are preferred. Especially preferred are polar solvents such as water and the alkanols, such as methanol, ethanol, propanol, isopropanol, butanol and t-butanol, and ethylene dichloride. Other similar inert solvents will be recognized by those skilled in the art of organic chemistry.

The recrystallization step is carried out satisfactorily at room temperatures. In most instances it may be preferable to heat the solution, such as to the boiling temperature, and then cool to promote crystallization. Such variations in the process are deemed well within the skill of those in the art and are not critical limitations on the process.

EXAMPLE 1

N-Acetyl-D-phenylalanine

To a stirred solution of 20.0 parts of D-phenylalanine in 121 parts of water, cooled to about 1°–2°, is added, portionwise, an aqueous 50% sodium hydroxide solution until pH 12 is reached. Then 37 parts of acetic anhydride is added, while continuously adding aqueous 50% sodium hydroxide to keep the pH at about 12 and cooling the solution to keep the temperature at between about 10° to 30°. After about 20 minutes the mixture is acidified to pH 1 with concentrated hydrochloric acid and filtered. The recovered solid is recrystallized from water to afford N-acetyl-D-phenylalanine, melting at about 170°–172°.

EXAMPLE 2

N-Propionyl-D-phenylalanine

By substituting an equivalent quantity of propionic anhydride in the procedure of Example 1, there is produced N-propionyl-D-phenylalanine.

EXAMPLE 3

N-n-Butyryl-D-phenylalanine

Substitution of an equivalent quantity of butyric anhydride in the procedure of Example 1 affords N-n-butyryl-D-phenylalanine.

EXAMPLE 4

N-Acetyl-D-phenylalanine.L-phenylalanine Methyl Ester 10.35 Parts of N-acetyl-D-phenylalanine is dissolved in 40 parts of methanol, then treated with 17.9 parts of DL-phenylalanine methyl ester. A precipitate forms immediately and an additional 60 parts of methanol is added. The mixture then is filtered and the solid remaining is washed with additional methanol and dried to yield the crude salt of N-acetyl-D-phenylalanine and L-phenylalanine methyl ester.

EXAMPLE 5

N-Acetyl-D-phenylalanine.L-Phenylalanine Ethyl Ester

Substitution of an equivalent quantity of DL-phenylalanine ethyl ester in the procedure of Example 4 and utilization of ethanol as solvent in place of the methanol described therein affords the salt of N-acetyl-D-phenylalanine and L-phenylalanine ethyl ester.

EXAMPLE 6

N-Propionyl-D-phenylalanine.L-Phenylalanine Methyl Ester

When an equivalent quantity of N-propionyl-D-phenylalanine is substituted in the procedure of Example 4, there is obtained the salt of N-propionyl-D-phenylalanine and L-phenylalanine methyl ester.

EXAMPLE 7

N-Acetyl-D-phenylalanine.L-Phenylalanine Methyl Ester

Utilization of water in place of methanol as the solvent in Example 4, and equivalent amounts of the sodium salt of N-acetyl-D-phenylalanine and hydrochloride salt of L-phenylalanine methyl ester affords the salt of N-acetyl-D-phenylalanine and L-phenylalanine methyl ester.

EXAMPLE 8

4.64 Parts of the crude salt comprised of 88.5% of the salt of N-acetyl-D-phenylalanine and L-phenylalanine methyl ester and 11.5% of the salt of N-acetyl-D-phenylalanine and D-phenylalanine methyl ester is suspended in 46 parts by volume of ethylene dichloride and heated to boiling. Then 0.48 part of DL-phenylalanine methyl ester is added and the mixture is boiled for 5 additional minutes, accompanied by continual stirring. Then the mixture is cooled in an ice bath and filtered. The recovered solid consists of 99.1% optically pure salt of N-acetyl-D-phenylalanine and L-phenylalanine methyl ester.

EXAMPLE 9

3.09 Parts of the crude salt as describe in Example 8 is suspended in 30 parts by volume of ethylene dichloride and heated to boiling. Then 0.158 part of L-phenylalanine methyl ester is added and an the resultant slurry is boiled for about 5 minutes, cooled to 0°C., and maintained at 0°C. for about 40 minutes. The solid, recovered by filtration, affords 98.1% optically pure salt of N-acetyl-D-phenylalanine and L-phenylalanine methyl ester.

EXAMPLE 10

By substituting equivalent quantities of crude salt of N-acetyl-D-phenylalanine and L-phenylalanine ethyl ester and DL-phenylalanine ethyl ester in the procedure of Example 8, there is obtained purified salt of N-acetyl-D-phenylalanine and L-phenylalanine ethyl ester.

EXAMPLE 11

When equivalent quantities of crude salt of N-propionyl-D-phenylalanine and L-phenylalanine methyl ester and DL-phenylalanine methyl ester are substituted in the procedure of Example 8, there is obtained purified salt of N-propionyl-D-phenylalanine and L-phenylalanine methyl ester.

EXAMPLE 12

4.64 Parts of the crude salt comprised of 88.9% of the salt of N-acetyl-D-phenylalanine and L-phenylalanine methyl ester and 11.1% of the salt of N-acetyl-D-phenylalanine and D-phenylalanine methyl ester is dissolved in a boiling mixture of 46 parts by volume of ethylene dichloride and 9.5 parts by volume of methanol. 0.47 Part of DL-phenylalanine methyl ester is added and the mixture is stirred for several minutes, then allowed to cool to room temperature over a period of about 1 hour. Further cooling at 0°C. yields a solid material, which is recovered by filtration, consisting of 99% optically pure salt of N-acetyl-D-phenylalanine and L-phenylalanine methyl ester.

EXAMPLE 13

4.0 Parts of the crude salt comprising 81.2% of the salt of N-acetyl-D-phenylalanine and L-phenylalanine methyl ester and 18.8% of the salt of N-acetyl-D-phenylalanine and D-phenylalanine methyl ester is slurried in 40 parts by volume of ethylene dichloride and heated to its boiling temperature. 0.7 Part of DL-phenylalanine methyl ester is added and the slurry is stirred at the boiling point for about 5 minutes. After cooling and filtering, the solid is recovered to yield purified salt of N-acetyl-D-phenylalanine and L-phenylalanine methyl ester of 98.5% optical purity.

EXAMPLE 14

Hydrochloride Salt of L-Phenylalanine Methyl Ester 0.5 Part of the salt of N-acetyl-D-phenylalanine and L-phenylalanine methyl ester is dissolved in 5 parts of hot water. Then 0.2 part by volume of concentrated hydrochloric acid is added and the mixture is filtered, thereby collecting the N-acetyl-D-phenylalanine solid and leaving crude L-phenylalanine methyl ester hydrochloride in the filtrate. The filtrate is evaporated to dryness, and the hydrochloride salt of L-phenylalanine methyl ester then is dissolved in water. Sodium carbonate is added, then ether. The ethereal extract is separated and acidified to yield the hydrochloride salt of L-phenylalanine methyl ester, which, upon recrystallization from methanol, exhibits an $[\alpha]_D$ at 2% in ethanol of about +35.7°.

EXAMPLE 15

Hydrochloride Salt of L-Phenylalanine Methyl Ester

A stirred solution of 2.0 parts of the salt of N-acetyl-D-phenylalanine and L-phenylalanine methyl ester in 20 parts of water is treated with 3.5 parts of potassium carbonate. An aqueous layer and an oily layer form and the mixture is extracted with ether. The aqueous layer, containing N-acetyl-D-phenylalanine, is separated and acidified with hydrochloric acid to yield, after cooling and filtering, N-acetyl-D-phenylalanine. The ethereal layer is dried over anhydrous sodium sulfate, then acidified with a hydrochloric acid-isopropanol mixture. The solid which forms is collected by filtration, then redissolved in methanol. Addition of ether affords crystals of the hydrochloride salt of L-phenylalanine methyl ester, displaying an $[\alpha]_D$ in 2% ethanol of about +35°. That product is the same as that obtained in Example 9.

EXAMPLE 16

By substituting equivalent quantities of the products of Examples 10 and 11 in the procedure of Example 15, there is afforded the hydrochloride salt of L-phenylalanine ethyl ester and the hydrochloride salt of L-phenylalanine methyl ester, respectively.

What is claimed is:

1. In a process for the production of L-phenylalanine alkyl ester from the corresponding DL-phenylalanine alkyl ester by resolving with an N-acyl-D-phenylalanine, the improvement which comprises recrystallizing in an inert solvent the crude salt of N-acyl-D-phenylalanine and L-phenylalanine alkyl ester in the presence of the corresponding DL-phenylalanine alkyl ester of L-phenylalanine alkyl ester.

2. The improvement as in claim 1 wherein the salt comprises compounds represented by the following formula

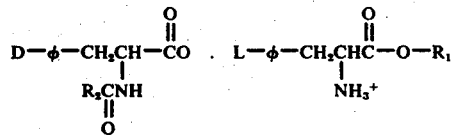

wherein $R_1$ is lower alkyl having 1–4 carbon atoms inclusive and $R_2$ is hydrogen or lower alkyl having 1–7 carbon atoms inclusive.

3. The improvement as in claim 1, wherein the salt comprises N-acetyl-D-phenylalanine and L-phenylalanine methyl ester and the recrystallization is in the presence of DL-phenylalanine methyl ester.

4. The improvement as in claim 1, wherein the salt comprises N-acetyl-D-phenylalanine and L-phenylalanine methyl ester and the recrystallization is in the presence of L-phenylalanine methyl ester.

* * * * *

UNITED STATES PATENT AND TRADEMARK OFFICE
CERTIFICATE OF CORRECTION

PATENT NO. : 3,983,162
DATED      : September 28, 1976
INVENTOR(S) : James M. Schlatter It is certified that error appears in the above-identified patent and that said Letters Patent are hereby corrected as shown below:

Column 1, line 37, "$r_2$" should read -- $R_2$ --.

Column 4, line 28, "describe" should read -- described --.

Column 4, line 32, "and an" should read -- and --.

Column 6, Claim 1, line 20, "of" should read -- or --.

Signed and Sealed this

Fourth Day of January 1977

[SEAL]

Attest:

RUTH C. MASON
*Attesting Officer*

C. MARSHALL DANN
*Commissioner of Patents and Trademarks*